United States Patent [19]

Ohmori et al.

[11] Patent Number: 5,475,033
[45] Date of Patent: Dec. 12, 1995

[54] ANTI-ALLERGIC PHARMACEUTICAL COMPOSITION FOR OPHTHALMIC TOPICAL ADMINISTRATION

[75] Inventors: Hitoshi Ohmori, Okayama; Takahiro Ogawa, Nishinomiya; Fuminori Tokumochi, Kobe; Atsushi Okumura, Nishinomiya, all of Japan

[73] Assignees: Taiho Pharmaceutical Co., Ltd, Tokyo; Senju Pharmaceutical Co., Ltd., Osaka, both of Japan

[21] Appl. No.: 241,719

[22] Filed: May 12, 1994

[30] Foreign Application Priority Data

May 14, 1993 [JP] Japan .................................. 5-112795

[51] Int. Cl.⁶ .................................................. A61K 31/16
[52] U.S. Cl. ........................................ 514/599; 514/912
[58] Field of Search .................................. 514/599, 912

[56] References Cited

U.S. PATENT DOCUMENTS

| | | | |
|---|---|---|---|
| 4,556,737 | 12/1985 | Koda et al. | 564/218 |
| 4,691,018 | 9/1987 | Mori et al. | 546/309 |

FOREIGN PATENT DOCUMENTS

| | | |
|---|---|---|
| 0090732 | 10/1983 | European Pat. Off. . |
| 0203435 | 12/1986 | European Pat. Off. . |
| 0499063 | 7/1992 | European Pat. Off. . |

OTHER PUBLICATIONS

Chemical Abstracts 118:116379 (1992). Matsuura et al.
Chemical Abstracts 117:204788 (1992). Togawa et al.
Tokumochi et al., Investigative Ophthalmology & Visual Sciences, vol. 35, No. 4, p. 1291 1994.
Koda et al., Agents and Actions Supplements, vol. 34 1991, pp. 369–378.

Primary Examiner—Zohreh Fay
Attorney, Agent, or Firm—Wenderoth, Lind & Ponack

[57] ABSTRACT

The present invention provides an anti-allergic pharmaceutical composition for ophthalmic topical administration comprising an IgE antibody production inhibitor as an active ingredient. The present invention also provides a process for producing an anti-allergic pharmaceutical composition for ophthalmic topical administration, which comprises mixing an IgE antibody production inhibitor with a pharmaceutically acceptable carrier, excipient or diluent.

8 Claims, 3 Drawing Sheets

Days after the immunization (days)

Days after the immunization (days)

ANTI-ALLERGIC PHARMACEUTICAL COMPOSITION FOR OPHTHALMIC TOPICAL ADMINISTRATION

FIELD OF THE INVENTION

The present invention relates to an anti-allergic pharmaceutical composition for ophthalmic topical administration. Specifically, the present invention relates to an anti-allergic pharmaceutical composition for ophthalmic topical administration comprising an IgE antibody production inhibitor.

BACKGROUND OF THE INVENTION

Allergic reactions include four types of reactions, i.e., types I, II, III and IV. The type I (immediate-type, anaphylactic) allergic reaction is associated with immunogiobulin E (hereinafter referred to as an IgE antibody). The reaction steps can be divided roughly into the following three steps. The first step is a sensitization step involving IgE antibody production and binding of the resulting IgE antibodies to mast cells or basophils. The second step involves degranulation of the mast cells or basophils and release of chemical mediators. The third step involves onset of effects of the released chemical mediators on the target organs. Thus, the type I allergic reaction against foreign antigens leads to onset of symptoms through the above reaction steps.

Only symptomatic treatments by inhibiting the above second and/or third reaction steps have been carried out to treat allergic diseases. That is, the treatments are carried out by inhibiting the release of chemical mediators accompanying the degranulation and/or by inhibiting allergic reactions induced by the released chemical mediators. These symptomatic treatments have been known to be effective not only in systemic administration of antiallergic agents but also in topical administration of them to eyes or the like. However, the effects of the treatments are limited because the treatments do not inhibit IgE antibody production which is the basic first step of the type I allergic reaction.

As fundamental remedies against the type I allergic reaction, medicaments inhibiting the above first step, namely IgE antibody production inhibitors are being developed. Examples of such inhibitors include (±)-{2-[4-(3-ethoxy-2-hydroxypropoxy)phenylcarbamoyl] ethyl}-dimethylsulfonium p-toluenesulfonate (hereinafter sometimes referred to as suplatast tosilate), ethyl 2,6-bis-(N-methylcarbamoyl)-pyridine- 4-carboxylate (hereinafter sometimes referred to as CS-1433) and the like. Anti-allergic effects of them in systemic administration, namely oral administration and the like have been reported (U.S. Pat. No. 4,556,737, New Current, Vol. 3, No. 26 (1992) etc. for suplatast tosilate; Allergy, Vol. 36, No. 8 (1987) etc. for CS-1433). However, there is no report the effects of these drugs in ophthalmic topical administration because the mechanisms of IgE antibody production by local sensitization is not clear.

As described above, there is no satisfactory anti-allergic agent effective in ophthalmic topical administration.

OBJECTS OF THE INVENTION

The main object of the present invention is to provide an excellent anti-allergic pharmaceutical composition for ophthalmic topical administration.

This object as well as other objects and advantages of the present invention will become apparent to those skilled in the art from the following description with reference to the accompanying drawings.

BRIEF EXPLANATION OF THE DRAWINGS

In FIG. 3, the symbols 1, 2 and 3 indicate the determinations for the following organs, respectively:

Figure 1:
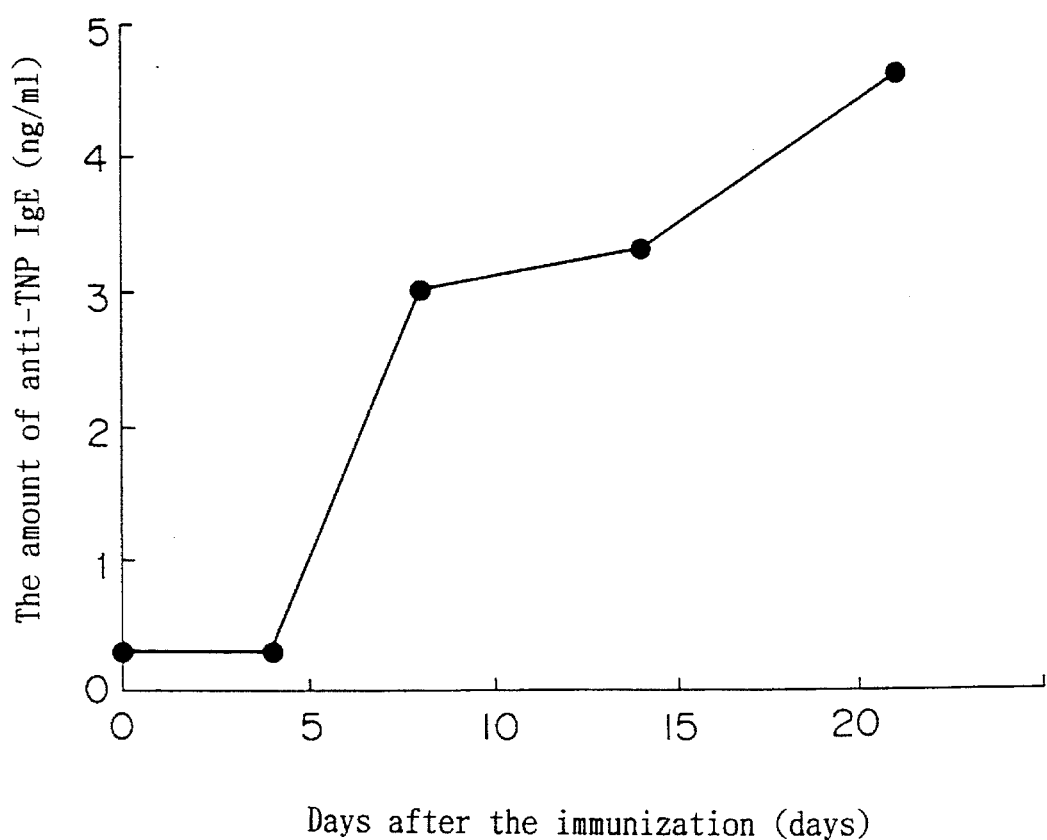
FIG. 1 is a graph showing changes of IgE antibody production in a parotic lymph node after mouse conjunctiva immunization with the passage of time. The abscissa indicates the number of days after the immunization. The ordinate indicates the amount of anti-TNP IgE (ng/ml).

1: parotic lymph node; 2: spleen; 3: mesenteric lymph node

SUMMARY OF THE INVENTION

The present inventors have intensively studied to obtain anti-allergic agents effective in ophthalmic topical administration based on the view that drugs are, in general, preferably administered topically considering the side effect, and that, if IgE antibodies are locally produced in eyes, ophthalmic topical administration is preferable to systemic administration considering the delivery of the drugs. As a result, it has firstly been found that IgE antibodies are produced only in lymph nodes near eyes (jugular lymph nodes, particularly parotic lymph node) by ophthalmic local immunization. After further studies based on this new finding, it has also been found that ophthalmic topical administration of the above IgE antibody production inhibitors surprisingly inhibits IgE antibody production by lymphocytes. Thus, the present invention has been completed.

In one aspect, the present invention provides a novel and useful anti-allergic pharmaceutical composition for ophthalmic topical administration comprising IgE antibody production inhibitors as an active ingredient.

Specifically, the present invention provides anti-allergic pharmaceutical compositions for ophthalmic topical administration comprising as an active ingredient (±)-{2-[4-(3-ethoxy-2-hydroxypropoxy)phenylcarbamoyl]ethyl}-dimethylsulfonium p-toluensulfonate (i.e., suplatast tosilate) of the formula (I):

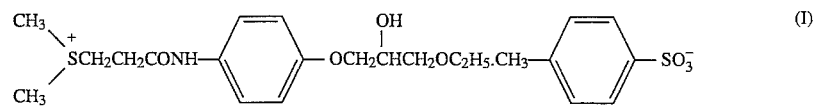

In another aspect, the present invention also provides a process for producing an anti-allergic pharmaceutical composition for ophthalmic topical administration, which comprises mixing an IgE antibody production inhibitor with a pharmaceutically acceptable carrier, excipient or diluent.

DETAILED DESCRIPTION OF THE INVENTION

Examples of the IgE antibody production inhibitors which are the active ingredients of the pharmaceutical compositions of the present invention include the above suplatast tosilate, CS-1433 and the like. The physical and chemical properties and the production are described, for example in U.S. Pat. No. 4,556,737, for suplatast tosilate and in U.S. Pat. No. 4,691,018, for CS-1433. Suplatast tosilate can be prepared, for example, by reacting (±)-{2-[4-( 3-ethoxy-2-hydroxypropoxy)phenylcarbamoyl]ethyl}methylsulfide with methyl p-toluenesulfonate (see U.S. Pat. No. 4,556,737). CS-1433 can be prepared, for example, by reacting triethyl pyridine-2,4,6-tricarboxylate with methylamine (see U.S. Pat. No. 4,691,018).

As is clear from the Experiments hereinafter, the IgE antibody production inhibitors have excellent IgE antibody production-inhibiting activity and can therefore be used for the anti-allergic pharmaceutical composition for ophthalmic topical administration of the present invention.

The pharmaceutical composition of the present invention can be produced, for example, by mixing an IgE antibody production inhibitor (e.g., suplatast tosilate) with per se known pharmaceutically acceptable carriers, excipients, diluents or the like and may be formulated into parenteral compositions such as eye-drops (ophthalmic solutions or suspensions), eye ointments or the like according to known methods.

When used as eye-drops, the anti-allergic pharmaceutical composition of the present invention may contain additives such as buffers, isotonizing agents, preservatives, pH adjustors, thickeners, chelating agents and the like which are conventionally used in eye-drops unless they are unsuited for the purpose of the present invention.

Examples of such buffers include phosphate buffers, borate buffers, citrate buffers, tartrate buffers, acetate buffers, amino acids and the like.

Examples of such isotonizing agents include saccharides such as sorbitol, glucose, mannitol and the like; polyhydric alcohols such as glycerin, polyethylene glycol, propylene glycol and the like; salts such as sodium chloride and the like.

Examples of such preservatives include benzalkonium chloride, benzethonium chloride, parahydroxybenzoates (e.g., methyl parahydroxybenzoate, ethyl parahydroxybenzoate, etc.), benzyl alcohol, phenethyl alcohol, sorbic acid or salts thereof, thimerosal, chlorobutanol and the like.

Examples of such pH adjustors include hydrochloric acid, acetic acid, phosphoric acid, sodium hydroxide, ammonium hydroxide and the like.

Examples of such thickeners include hydroxyethylcellulose, hydroxypropylcellulose, methylcellulose, hydroxypropylmethylcellulose, carboxymethylcellulose and salts thereof, and the like.

Examples of such chelating agents include disodium edetate, sodium citrate, condensed sodium phosphate and the like.

When the anti-allergic pharmaceutical composition of the present invention is used as an eye ointment, examples of the eye ointment base include purified lanolin, petrolatum, plastibase, liquid paraffin and the like.

The anti-allergic pharmaceutical composition of the present invention may contain one or more other anti-allergic agent unless they are unsuited for the purpose of the present invention.

Further, the anti-allergic pharmaceutical composition of the present invention may contain other ingredients having other pharmacological activity in addition to the IgE antibody production inhibitor used in the present invention unless they are unsuited for the purpose of the present invention.

The pharmaceutical composition of the present invention can be administered topically to eyes of mammals (e.g., humans, rabbits, dogs, cats, cattle, horses, monkeys, etc.) with an allergic disease such as allergic conjunctivitis, vernal kerato conjunctivitis, pollinosis, etc.

The dose of the anti-allergic pharmaceutical composition of the present invention can appropriately be selected depending upon the administration route, symptoms, age and weight of the patient and the like. For example, when the pharmaceutical composition is administered to an adult human patient with an allergic disease, preferably, one to several drops of the composition in the form of eye-drops containing suplatast tosilate as an active ingredient in an amount of 0.01 to 10.0 w/v %, preferably 0.05 to 5.0 w/v %, more preferably 0.2 to 2.0 w/v % is administered 1 to 6 times a day depending upon the symptoms. In the case of the pharmaceutical composition in the form of eye ointments, the composition containing suplatast tosilate as an active ingredient in an amount of 0.01 to 10 w/w %, preferably 0.1 to 5 w/w % is preferably administered 1 to 6 times a day depending upon the symptoms.

The following examples further illustrate the present invention in detail and the following experiments show effects of the present invention, but are not to be construed to limit the scope thereof.

EXAMPLE 1

Eye-drops (ophthalmic solution)

According to a conventional method, an ophthalmic solution having the following formulation was prepared.

| Ingredients | Amounts |
| --- | --- |
| Suplatast tosilate | 2.0 g |
| Sodium chloride | 0.9 g |
| Sodium dihydrogenphosphate | 0.1 g |
| Benzalkonium chloride | 0.005 g |
| Sodium hydroxide | suitable amount (pH 6.0) |

Sterile purified water was added to a total volume of 100 ml.

EXAMPLE 2

Eye-drops (ophthalmic solution)

According to a conventional method, an ophthalmic solution having the following formulation was prepared.

| Ingredients | Amounts |
| --- | --- |
| Suplatast tosilate | 0.5 g |
| Conc. glycerin | 2.6 g |
| Sodium acetate | 0.1 g |

-continued

| Ingredients | Amounts |
| --- | --- |
| Benzalkonium chloride | 0.005 g |
| Diluted hydrochloric acid | suitable amount (pH 5.0) |

Sterile purified water was added to a total volume of 100 ml.

EXAMPLE 3

Eye-drops (ophthalmic solution)

According to a conventional method, an ophthalmic solution having the following formulation was prepared.

| Ingredients | Amounts |
| --- | --- |
| Suplatast tosilate | 0.5 g |
| Mannitol | 5.0 g |
| Sodium acetate | 0.1 g |
| Chlorobutanol | 0.2 g |
| Benzethonium chloride | 0.005 g |
| Diluted hydrochloric acid | suitable amount (pH 4.0) |

Sterile purified water was added to a total volume of 100 ml.

EXAMPLE 4

Eye-drops (ophthalmic solution)

According to a conventional method, an ophthalmic solution having the following formulation was prepared.

| Ingredients | Amounts |
| --- | --- |
| Suplatast tosilate | 1.0 g |
| Conc. glycerin | 2.6 g |
| Sodium acetate | 0.05 g |
| Hydroxypropylmethylcellulose | 0.1 g |
| Methyl parahydroxybenzoate | 0.02 g |
| Propyl parahydroxybenzoate | 0.01 g |
| Diluted hydrochloric acid | suitable amount (pH 5.5) |

Sterile purified water was added to a total volume of 100 ml.

EXAMPLE 5

Eye-drops (ophthalmic solution)

According to a conventional method, an ophthalmic solution having the following formulation was prepared.

| Ingredients | Amounts |
| --- | --- |
| Suplatast tosilate | 0.3 g |
| Sodium chloride | 0.9 g |
| Sodium citrate | 0.02 g |
| Methyl parahydroxybenzoate | 0.02 g |
| Chlorobutanol | 0.1 g |
| Acetic acid | suitable amount (pH 4.5) |

Sterilized purified water was added to a total volume of 100 ml.

EXAMPLE 6

Eye ointment

According to a conventional method, an eye ointment having the following formulation was prepared.

| Ingredients | Amounts |
| --- | --- |
| Suplatast tosilate | 1.0 g |
| Liquid paraffin | 1.0 g |
| White soft paraffine | suitable amount Total 100 g |

EXAMPLE 7

Eye-drops (ophthalmic solution)

According to a conventional method, an ophthalmic solution having the following formulation was prepared.

| Ingredients | Amounts |
| --- | --- |
| Suplatast tosilate | 2.0 g |
| Conc. glycerin | 2.6 g |
| Sodium dihydrogenphosphate | 0.1 g |
| Benzalkonium chloride | 0.005 g |
| Sodium hydroxide | suitable amount (pH 6.0) |

Sterile purified water was added to a total volume of 100 ml.

EXAMPLE 8

Eye-drops (ophthalmic solution)

According to a conventional method, an ophthalmic solution having the following formulation was prepared.

| Ingredients | Amounts |
| --- | --- |
| Suplatast tosilate | 0.5 g |
| Sodium chloride | 0.9 g |
| Sodium acetate | 0.1 g |
| Benzalkonium chloride | 0.005 g |
| Diluted hydrochloric acid | suitable amount (pH 4.5) |

Sterile purified water was added to a total volume of 100 ml.

Experiment 1

Figure 2:
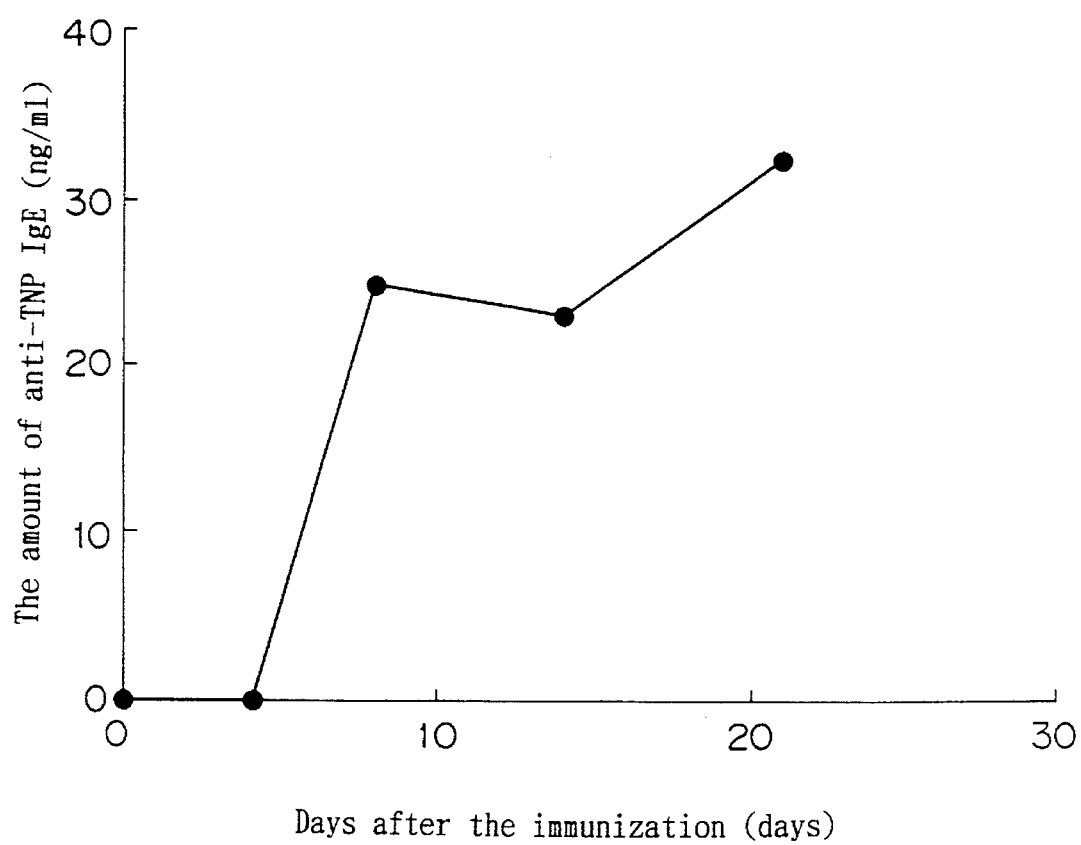
FIG. 2 is a graph showing changes of the production of IgE antibodies in serum secreted from removed lymph node cells. The abscissa indicates the number of days (day) after immunization. The ordinate indicates the amount of anti-TNP IgE (ng/ml).
Figure 3:
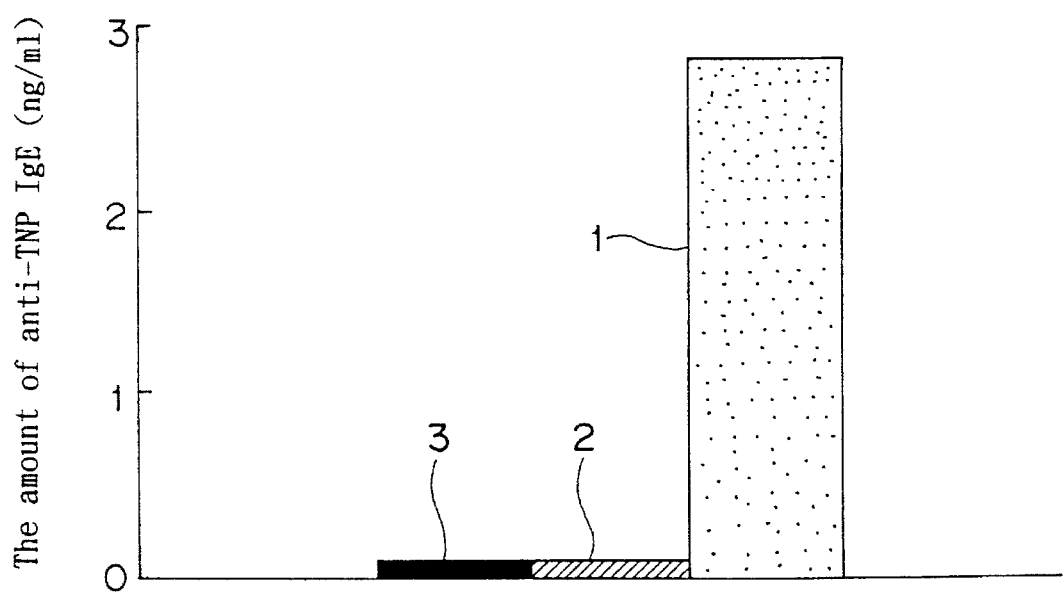
FIG. 3 is a graph showing IgE antibody production in various lymph node cells such as parotic lymph node cells, spleen cells and mesenteric lymph node cells. The ordinate indicates the amount of anti-TNP IgE (ng/ml).

Changes of IgE antibody production in a parotic lymph node after mouse conjunctiva immunization with the passage of time For immunization, physiological saline (10 µl) containing dinitrophenylated ascaris extract (hereinafter referred to as DNP-As)(4 µg) and aluminium hydroxide gel (hereinafter referred to as Alum)(60 µg) was injected into a palpebralis subconjunctival part of the right eye of a BALB/c female mouse using a 27 G needle. Then, the parotic lymph node, spleen and mesenteric lymph node were removed. The cells ($2\times10^6$) from these organs were incubated in Roswell Park Memorial Institute (RPMI) 1640 medium (0.2 ml) for 4 days. The secreted anti-dinitrophenyl IgE was determined as anti-trinitrophenyl (hereinafter referred to as anti-TNP) IgE by Enzyme-linked Immunosorbent Assay (ELISA). The results are shown in FIG. 1. The amount of IgE antibodies in the serum was also determined with the passage of time. The results are shown in FIG. 2. Further, the amount of IgE antibodies produced in various lymph node organs (parotic lymph nodes, spleen, mesenteric lymph nodes) was determined. The results are shown in FIG. 3.

From the above results, it has been found that IgE antibody production by ophthalmic local immunization occurs only in the parotic lymph node (see FIG. 3) and the IgE antibody production begins to increase suddenly at about the 8th day (see FIG. 1 and FIG. 2). It means that, in order to screen drugs exhibiting IgE antibody production-inhibiting activity by ophthalmic topical administration, we have only to determine IgE antibodies produced by the neighboring lymph node cells. It also means that IgE antibodies are preferably determined at least 8 days after the immunization.

Experiment 2

Effects of suplatast tosilate on IgE antibody production in mice

Animals:

BALB/c female mice (111 mice, body weight: about 15 g) were used.

Test drugs and groups of mice:

The above 111 mice were grouped into the following six groups:

Physiological saline (eye-drops) administered group (20 mice);

0.05 w/v % suplatast tosilate (eye-drops) administered group (18 mice);

0.2 w/v % suplatast tosilate (eye-drops) administered group (19 mice);

0.5 w/v % suplatast tosilate (eye-drops) administered group (19 mice);

2.0 w/v % suplatast tosilate (eye-drops) administered group (19 mice); and

Suplatast tosilate (5 mg/kg) orally administered group (16 mice).

Administration of the test drugs:

To the eye-drops administered groups, the test drugs were dropped in the right eyes for 20 days beginning 5 days before the immunization 4 times a day in a dose of 4 µl per administration. To the orally administered group, the drug was orally administered to each mouse once a day in a dose of 100 µl per administration.

Immunization:

Physiological saline (10 µl) containing DNP-As (4 µg) and Alum (60 µg) was injected into a palpebralis subconjunctival part of the right eye of each mouse using a 27 G needle.

Assay: 10 Each mouse was sacrificed 14 days after the immunization. The right parotic lymph node was removed and blood (200 µl) was taken. In each of the groups, the parotic lymph node was cultured per mouse, passed through a mesh while washing it well with Minimum Essential Medium (hereinafter referred to as MEM), and centrifuged at 1500 rpm for 5 minutes. RPMI 1640 medium (450 µl) was added to the resulting precipitate, and 200 µl of the mixture was put into wells and cultured for 4 days. IgE antibodies were determined in duplicate by the bead method. The blood was stored under freezing after separation of serum, and assayed for the IgE antibodies simultaneously with the other samples.

The results are shown in Table 1 for the parotic lymph nodes and in Table 2 for the serum.

TABLE 1

The amount of IgE antibodies in parotic lymph nodes

| Administered test drug (Administration route) | Anti-TNP IgE (ng/ml) | Number of examples |
|---|---|---|
| Physiological saline (eye-drops) | 5.11 ± 0.63 | 20 |
| 0.05 w/v % suplatast tosilate (eye-drops) | 4.22 ± 0.51 | 18 |
| 0.2 w/v % suplatast tosilate (eye-drops) | 2.87 ± 0.43** | 19 |
| 0.5 w/v % suplatast tosilate (eye-drops) | 2.34 ± 0.34** | 19 |
| 2.0 w/v % suplatast tosilate (eye-drops) | 3.08 ± 0.50* | 19 |
| Suplatast tosilate (5 mg/kg) (orally) | 5.85 ± 0.58 | 16 |

Note)
In the above table, each value indicates mean ± standard error.
The marks "*" and "**" indicate that there is a significant difference from the control.
*: $P < 0.05$, **: $P < 0.01$.

TABLE 2

The amount of IgE antibodies in the serum

| Administered test drug (Administration route) | Anti-TNP IgE (ng/ml) | Number of examples |
|---|---|---|
| Physiological saline (eye-drops) | 58.8 ± 8.8 | 20 |
| 0.05 w/v% suplatast tosilate (eye-drops) | 64.1 ± 10.4 | 18 |
| 0.2 w/v% suplatast tosilate (eye-drops) | 57.5 ± 9.1 | 19 |
| 0.5 w/v% suplatast tosilate (eye-drops) | 54.3 ± 7.2 | 19 |
| 2.0 w/v% suplatast tosilate (eye-drops) | 65.1 ± 11.8 | 19 |
| Suplatast tosilate (5 mg/kg) (orally) | 59.7 ± 7.0 | 16 |

Note)
In the above table, each value indicates mean ± standard error.

As is clear from the results shown in Table 1, the suplatast tosilate (eye-drops) showed significant IgE antibody production inhibiting activity in such a low concentration as 0.2 to 0.5 w/v % in parotic lymph nodes. On the other hand, the suplatast tosilate (orally) showed no significant IgE antibody production inhibiting activity even in a dose of 5 mg/kg which corresponds to the concentration of the 0.5 w/v % suplatast tosilate (eye-drops). Further, as is clear from the results shown in Table 2, the IgE antibody levels in the serum were not affected in any concentrations in the suplatast tosilate (eye-drops) and suplatast tosilate (orally). These results show that the IgE antibody production by ophthalmic local immunization occurs in parotic lymph nodes (see Experiment 1) and suplatast tosilate exhibits excellent IgE antibody production inhibiting activity only in ophthalmic topical administration.

Experiment 3

Acute toxicity test of suplatast tosilate

Male ddy mice weighing about 20 g were used. A solution of suplatast tosilate in physiological saline was injected intraperitoneally. The 50% lethal dose ($LD_{50}$: mg/kg) was determined by the up-down method. The results showed that the $LD_{50}$ of suplatast tosilate was 254 mg/kg.

What is claimed is:

1. A method of treating an allergic disease in mammals which comprises topically administering to an eye of a subject in need thereof an effective amount of an IgE antibody production inhibitor compound of the following formula:

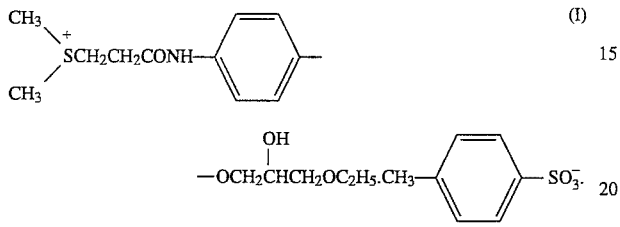

2. A method according to claim 1, wherein the IgE antibody production inhibitor is formulated into eye-drops.

3. A method according to claim 1, wherein the IgE antibody production inhibitor is formulated into eye ointments.

4. A method according to claim 1, wherein the compound of the formula (I) is formulated into eye-drops.

5. A method according to claim 1, wherein the compound of the formula (I) is formulated into eye ointments.

6. A method according to claim 4, wherein the compound of the formula (I) in an amount of 0.01 to 10.0 w/v % is administered.

7. A method according to claim 4, wherein the compound of the formula (I) in an amount of 0.05 to 5.0 w/v % is administered.

8. A method according to claim 4, wherein the compound of the formula (I) in an amount of 0.2 to 2.0 w/v % is administered.

* * * * *